(12) United States Patent
Zhuang et al.

(10) Patent No.: US 7,975,555 B2
(45) Date of Patent: Jul. 12, 2011

(54) APPARATUS FOR SIMULTANEOUSLY MEASURING LONGITUDINAL AND SHEAR WAVE SPEEDS IN MATERIALS UNDER COMPRESSION LOAD VIA AN ULTRASONIC TRANSDUCER

(75) Inventors: Shiming Zhuang, Menasha, WI (US); Guruswami Ravichandran, Arcadia, CA (US); Theresa Kidd, Vienna, VA (US)

(73) Assignee: California Institute of Technology, Pasadena, CA (US)

( * ) Notice: Subject to any disclaimer, the term of this patent is extended or adjusted under 35 U.S.C. 154(b) by 1257 days.

(21) Appl. No.: 11/607,838

(22) Filed: Dec. 1, 2006

(65) Prior Publication Data

US 2010/0275693 A1    Nov. 4, 2010

Related U.S. Application Data

(60) Provisional application No. 60/741,524, filed on Dec. 1, 2005.

(51) Int. Cl.
*G01N 3/04* (2006.01)
*G01L 1/16* (2006.01)

(52) U.S. Cl. ............... 73/778; 73/816; 73/846; 73/860; 73/597; 73/599

(58) Field of Classification Search ............... 73/597, 73/598, 599, 632, 645, 646, 778, 801, 816, 73/817, 846, 855, 856, 860, 866.5
See application file for complete search history.

(56) References Cited

U.S. PATENT DOCUMENTS 3,537,541 A * 11/1970 Moore et al. ............... 73/597
3,995,501 A * 12/1976 Wiley ............... 73/597
5,178,005 A * 1/1993 Peterson ............... 73/152.11
5,265,461 A * 11/1993 Steiger et al. ............... 73/38

(Continued)

FOREIGN PATENT DOCUMENTS

EP    1060367    9/2003

(Continued)

OTHER PUBLICATIONS

Ashman, R.B., Antich, P.P., Gonzales, J., Anderson, J., Rho, J., "A comparison of reflection and transmission . . . "J. Biomechanics, vol. 27, No. 9 pp. 1195-1199, 1994.
Freemantle R J and Challis R E 1998, "Combined compression and shear wave ultrasonic measurements on curing adhesive", Meas. Sci. Technol. 9 1291-302.

(Continued)

*Primary Examiner* — Hezron Williams
*Assistant Examiner* — Rose M Miller
(74) *Attorney, Agent, or Firm* — Tope-McKay & Associates

(57) ABSTRACT

An apparatus for simultaneously measuring longitudinal and shear wave speeds in materials under load via echo or transmission is described. The apparatus comprises a housing with an open end, a closed end opposite the open end with a hole in the closed end, and a housing exit port. A spacer resides inside the housing, the spacer having a spacer specimen side and a spacer transducer side. A load transferring body having a transducer hole fits inside the housing and contacts an interior surface of the housing. An ultrasonic transducer fits inside the transducer hole of the load transferring body. A transducer depressing mechanism secures the ultrasonic transducer against the spacer transducer side, whereby users can simultaneously measure longitudinal and shear wave speeds of specimens inserted into the hole in the closed end of the housing and contacting the spacer.

7 Claims, 8 Drawing Sheets

U.S. PATENT DOCUMENTS

| | | | |
|---|---|---|---|
| 5,533,402 | A | 7/1996 | Sarvazyan et al. |
| 6,221,019 | B1 | 4/2001 | Kantorovich et al. |
| 6,367,331 | B1 | 4/2002 | Murray et al. |
| 6,655,213 | B1 * | 12/2003 | Reinhardt et al. ............ 73/597 |
| 7,112,173 | B1 | 9/2006 | Kantorovich et al. |
| 2004/0220465 | A1 | 11/2004 | Cafarella |
| 2006/0193422 | A1 | 8/2006 | Davis et al. |
| 2006/0291608 | A1 | 12/2006 | Davis et al. |

FOREIGN PATENT DOCUMENTS

| | | |
|---|---|---|
| EP | 873516 | 12/2005 |
| WO | WO9713145 | 4/1997 |
| WO | WO9945348 | 9/1999 |
| WO | WO2004/062467 A2 | 7/2004 |

OTHER PUBLICATIONS

Nieminen, HJ, Toyras, J, Laasanen, MS, Jurvelin, JS, 2006, "Acoustic properties of articular cartilage under mechanical stress", Biorheology, vol. 43, 523-535 (Abstract Only).

Ohtani, T, Nishiyama, K, Yoshikawa, S, Ogi, H, Hirao, M, "Ultrasonic attenuation and microstructural evolution . . . " 2006, Materials Science and Engineering A, vol. 442, 466-470.

Walter, M.E. and Ravichandran, G. 1995, "An Experimental Investigation of Damage Evolution in a Ceramic . . . ", J. of Engineering Materials and Technology, vol. 117 pp. 101-108.

Ashman R. Corin, J. Turner, C., 1987 "Elastic Properties of Cancellous Bone Measurement by an Ultrasonic Technique," J. Biomechanics, vol. 20 No. 10, pp. 979-986.

* cited by examiner

APPARATUS FOR SIMULTANEOUSLY MEASURING LONGITUDINAL AND SHEAR WAVE SPEEDS IN MATERIALS UNDER COMPRESSION LOAD VIA AN ULTRASONIC TRANSDUCER

PRIORITY CLAIM

The present application is a non-provisional utility patent application, claiming the benefit of priority of U.S. Provisional Patent Application No. 60/741,524, filed Dec. 1, 2005, entitled "NOVEL METHOD FOR SIMULTANEOUSLY MEASURING THE LONGITUDINAL AND SHEAR WAVE SPEEDS IN A MATERIAL UNDER COMPRESSION LOAD."

GOVERNMENT RIGHTS

This invention was made with Government support under a contract from the Office of Naval Research, Grant No. N000140510202. The Government has certain rights in this invention.

BACKGROUND OF THE INVENTION (1) Field of the Invention

The present invention relates to a novel method and device for measuring longitudinal and shear wave speeds in materials and, more particularly, to a novel method and device for measuring longitudinal and shear wave speeds in materials when they are under load.

(2) Background of the Invention

Ultrasonic testing is a widely used method for investigating the properties of various materials. In the standard test method, separate longitudinal and shear transducers are used to measure the longitudinal and the shear wave speeds in a material. This device is unique because it only requires a pair of shear transducers to achieve the same measurements. The wave speed measurements are done either using the transducers in transmission mode or in echo mode. Both wave speeds are necessary to determine the first order elastic constants of a material. Ultrasonic testing is the most sophisticated and widely used tool for characterizing elastic properties of crystalline materials. However, the characterization of foam-like materials, especially when the materials are subjected to a compression load, using ultrasonic testing presents new challenges due to the high attenuation of ultrasound within these materials. This invention specifically addresses these issues making the in situ ultrasonic testing of foams and other cellular materials possible.

What is needed in the art is a device that measures the mechanical properties of materials that are being deformed and damaged, protects the transducers from damage, allows for ultrasonic testing of a material under a compression load, and facilitates the interchanging of test samples. In addition, a continuing need exists for a method that allows one to fully characterize the mechanical properties of a material without using multiple transducers. The aforementioned needs are novel features of the present invention.

SUMMARY OF INVENTION

The present invention relates to a general method for simultaneously measuring longitudinal and shear wave speeds in materials under load via echo. This process proceeds as a set of simple acts. The user loads a specimen, either compressionally, tensilely, or torsionally and the loading is directed along a loading axis. The user connects a transducer with the specimen without loading the transducer and connects the transducer with a data collection apparatus. An ultrasonic pulse is launched from the transducer into the specimen along the loading axis, simultaneously triggering the data collection apparatus. The user measures an echo signature on the data collection apparatus and identifies a leading echo group and a trailing echo group in the echo signature. The user then assigns a longitudinal effective delay to the leading echo group and a shear effective delay to the trailing echo group. Next a longitudinal wave speed is calculated from the longitudinal effective delay and a shear wave speed from the shear effective delay, whereby both longitudinal wave speeds and shear wave speeds of a specimen under load can be measured simultaneously using one transducer.

The present invention also discloses a method, analogous to the one described in the above paragraph, for measuring longitudinal and shear wave speed in materials under load via transmission.

In another aspect, the ultrasonic pulse is a shear wave.

In yet another aspect, the ultrasonic pulse is a longitudinal wave.

In yet another aspect, the ultrasonic pulse from the transducer impinges on the specimen at a substantially normal angle of incidence.

In yet another aspect, the ultrasonic pulse from the transducer impinges on the specimen at a substantially oblique angle of incidence.

The present invention also discloses a device for simultaneously measuring longitudinal and shear wave speeds in materials under load. The device comprises a rigid housing with a long axis. The body of the rigid housing is substantially parallel to the long axis; the body also possesses an exterior surface and an interior surface, an open end, and a closed end. The closed end is substantially opposite the open end and a hole is made in the closed end extending through the interior surface and the exterior surface. The closed end is substantially perpendicular to the long axis. A housing exit port is made in the body of the rigid housing, extending through the interior surface and the exterior surface. A spacer resides inside the rigid housing, the spacer having a spacer specimen side and a spacer transducer side substantially parallel to the spacer specimen side. The spacer is substantially larger than the hole in the closed end of the rigid housing. The spacer further contacts the interior surface of the rigid housing such that the closed end of the housing is in contact with the spacer specimen side. A load transferring body fits substantially inside the rigid housing. The load transferring body having an exterior, the entirety of the exterior of the load transferring body making substantially close contact with the interior surface of the body of the rigid housing. The load transferring body further has a transducer hole extending fully through the load transferring body and substantially parallel to the long axis of the rigid housing. The load transferring body also has a load transferring body exit port extending from the transducer hole fully through the load transferring body. An ultrasonic transducer fits substantially inside the transducer hole of the load transferring body, and a transducer depressing mechanism secures the ultrasonic transducer against the spacer transducer side. Thus, users can simultaneously measure longitudinal and shear wave speeds of specimens inserted into the hole in the closed end of the rigid housing and contacting the spacer. The user employs external load frames to load specimens between the spacer and an external supporting mechanism by applying load to the load transferring body; this happens without applying load to the ultrasonic transducer because there is no continuous load path to the ultrasonic transducer. The ultrasonic transducer sends ultrasonic pulses into the specimen through the spacer, detecting echoes of the ultrasonic pulses with the ultrasonic transducer or transmission of the ultrasonic pulses with external ultrasonic receivers. Users further run any connections, electrical or otherwise, to or from the ultrasonic transducer out of the housing exit port and the load transferring body exit port.

In yet another aspect, another, substantially identical device is located substantially opposite the device. This allows a user to simultaneously measure longitudinal and shear wave speeds of specimens, provided that such specimens are inserted into the holes in the closed ends of the rigid housings of both devices and are contacting the spacers of both devices. A user employs external load frames to load specimens between the spacers and applies load to the load transferring bodies without applying load to the ultrasonic transducers because there is no continuous load path to the ultrasonic transducers. The ultrasonic transducers send ultrasonic pulses into the specimen through the spacers, detecting echoes of the ultrasonic pulses with the ultrasonic transducers or transmission of the ultrasonic pulses with the ultrasonic transducers used as receivers. Users further run any connections, electrical or otherwise, to or from the ultrasonic transducers out of the housing exit ports and the load transferring body exit ports.

In yet another aspect, no load is applied to the specimen.

In yet another aspect, the rigid housing is a right-circular cylinder, the load transferring body is a right-circular cylinder, and the spacer is a right-circular cylinder.

In yet another aspect, the transducer depressing mechanism is a spring inserted into the transducer hole of the load transferring body such that the ultrasonic transducer is between the spring and the spacer. The device further comprises a set-screw, the set-screw is removably threaded into the transducer hole of the load transferring body. The user adjusts the set-screw to compress the spring against the ultrasonic transducer, holding the ultrasonic transducer firmly against the spacer transducer side.

In yet another aspect, the transducer depressing mechanism is electromagnetic.

In yet another aspect, the transducer depressing mechanism is pneumatic, whereby the transducer hole of the load transferring body is substantially sealed and gas is selectively injected into the hole, using gas pressure to hold the ultrasonic transducer firmly against the spacer.

In yet another aspect, the transducer depressing mechanism is a piezoelectric element inserted into the transducer hole of the load transferring body such that the ultrasonic transducer is between the piezoelectric element and the spacer. The device further comprises a set screw removably threaded into the transducer hole of the load transferring body. Users adjust the set screw until applying a voltage to the piezoelectric element causes the piezoelectric element to apply a force to the ultrasonic transducer and the set screw, thereby holding the ultrasonic transducer firmly against the spacer.

In yet another aspect, the ultrasonic transducer produces shear waves.

In yet another aspect, the ultrasonic transducer produces longitudinal waves.

BRIEF DESCRIPTION OF THE DRAWINGS

The objects, features and advantages of the present invention will be apparent from the following detailed descriptions of the various aspects of the invention in conjunction with reference to the following drawings, where.

DETAILED DESCRIPTION

The present invention relates to a novel method and device for measuring longitudinal and shear wave speeds in materials and, more particularly, to a novel method and device for measuring longitudinal and shear wave speeds in materials when they are under load. The following description is presented to enable one of ordinary skill in the art to make and use the invention and to incorporate it in the context of particular applications. Various modifications, as well as a variety of uses in different applications will be readily apparent to those skilled in the art, and the general principles defined herein may be applied to a wide range of embodiments. Thus, the present invention is not intended to be limited to the embodiments presented, but is to be accorded the widest scope consistent with the principles and novel features disclosed herein.

In the following detailed description, numerous specific details are set forth in order to provide a more thorough understanding of the present invention. However, it will be apparent to one skilled in the art that the present invention may be practiced without necessarily being limited to these specific details. In other instances, well-known structures and devices are shown in block diagram form, rather than in detail, in order to avoid obscuring the present invention.

The reader's attention is directed to all papers and documents which are filed concurrently with this specification and which are open to public inspection with this specification, and the contents of all such papers and documents are incorporated herein by reference. All the features disclosed in this specification, (including any accompanying claims, abstract, and drawings) may be replaced by alternative features serving the same, equivalent or similar purpose, unless expressly stated otherwise. Thus, unless expressly stated otherwise, each feature disclosed is one example only of a generic series of equivalent or similar features.

Furthermore, any element in a claim that does not explicitly state "means for" performing a specified function, or "step for" performing a specific function, is not to be interpreted as a "means" or "step" clause as specified in 35 U.S.C. Section 112, Paragraph 6. In particular, the use of "step of" or "act of" in the claims herein is not intended to invoke the provisions of 35 U.S.C. 112, Paragraph 6.

Please note, if used, the labels left, right, front, back, top, bottom, forward, reverse, clockwise and counter clockwise have been used for convenience purposes only and are not intended to imply any particular fixed direction. Instead, they are used to reflect relative locations and/or directions between various portions of an object.

(2) Description

Figure 1:
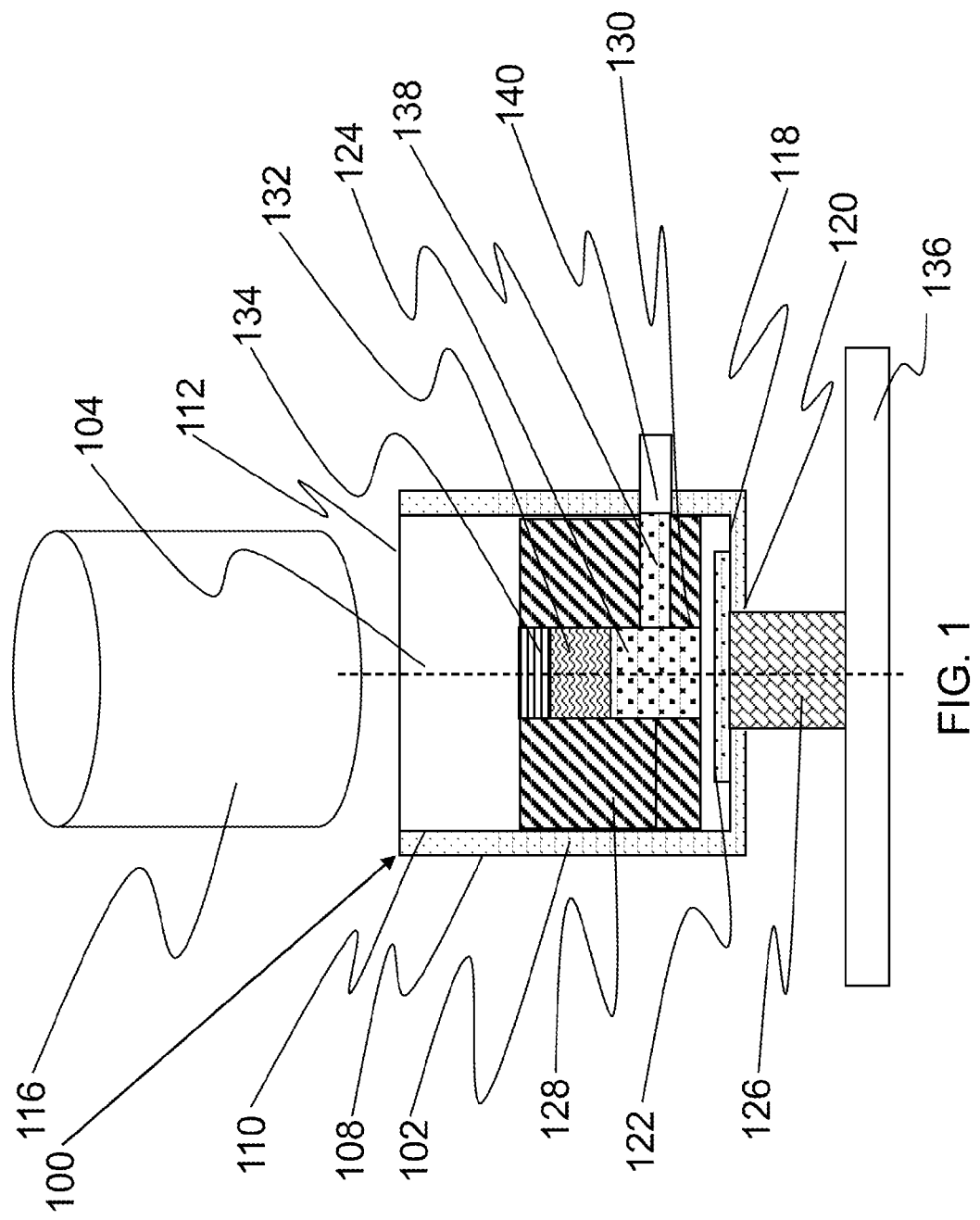
FIG. 1 is an illustration of an example of the echo mode testing device of the present invention showing the basic unit of the invention being used with a single transducer.

As shown in FIG. 1, a test device 100 is composed of a rigid housing 102 having a long axis 104, a body exterior surface 108 and an interior surface 110, an open end 112 with a hole that fits around an external load frame 116 or loading platen, and a closed end 118 with a smaller hole 120 which is covered by a spacer 122. Non-limiting material choices for the rigid housing 102 could be steel, aluminum, or tungsten carbide. As can be appreciated by one in the art, the geometry of the rigid housing 102 is arbitrary, but a cylindrical shape is an excellent choice as it is less prone to stress-induced failure than, for example, a rectangular prism. The spacer 122 may be made of any of a variety of materials as well, non-limiting examples of which include silicon carbide, tungsten carbide, aluminum, and steel. As can be appreciated by one in the art, the spacer 122 material can be chosen to impedance match the ultrasonic transducer 124 to the spacer 122 and the spacer 122 to the specimen 126. Inside the rigid housing 102 is a load-transferring body 128 which may be selected from any of a variety of materials, non-limiting examples of which include but are not limited to steel, aluminum, and tungsten carbide. A transducer hole 130 is bored in the load transferring body 128 which holds and protects the ultrasonic transducer 124. The loading force from the loading platen is transferred through the load transferring body 128 and spacer 122 to the specimen 126, while leaving the ultrasonic transducer 124 free of loading. Loading is any external force applied to the specimen 126; non-limiting examples of loading types include compression, tension, shear, torsion, and combinations thereof.

The spring 132 backing the ultrasonic transducer 124, a unique and novel feature, allows the ultrasonic transducer 124 to maintain contact with the spacer 122 without being damaged while the sample is being loaded. A setscrew 134 holds the spring in place. As can be appreciated by one in the art, any transducer depressing mechanism can be used to maintain contact between the ultrasonic transducer 124 and the spacer 122, non-limiting examples of which include gas pressure, electromagnetic actuators, piezoelectric elements, magnetism, and hydraulics.

The housing exit port 138 is aligned with the body exit port 140 to allow users to have access, electrical or otherwise, to the transducer.

FIG. 1 also shows the device of the present invention used in conjunction with an external support mechanism 136 which serves two purposes: first, it provides a stable surface for counterbalancing any forces produced while loading the sample; second, it forms a reflection interface with the specimen 126.

Figure 2:
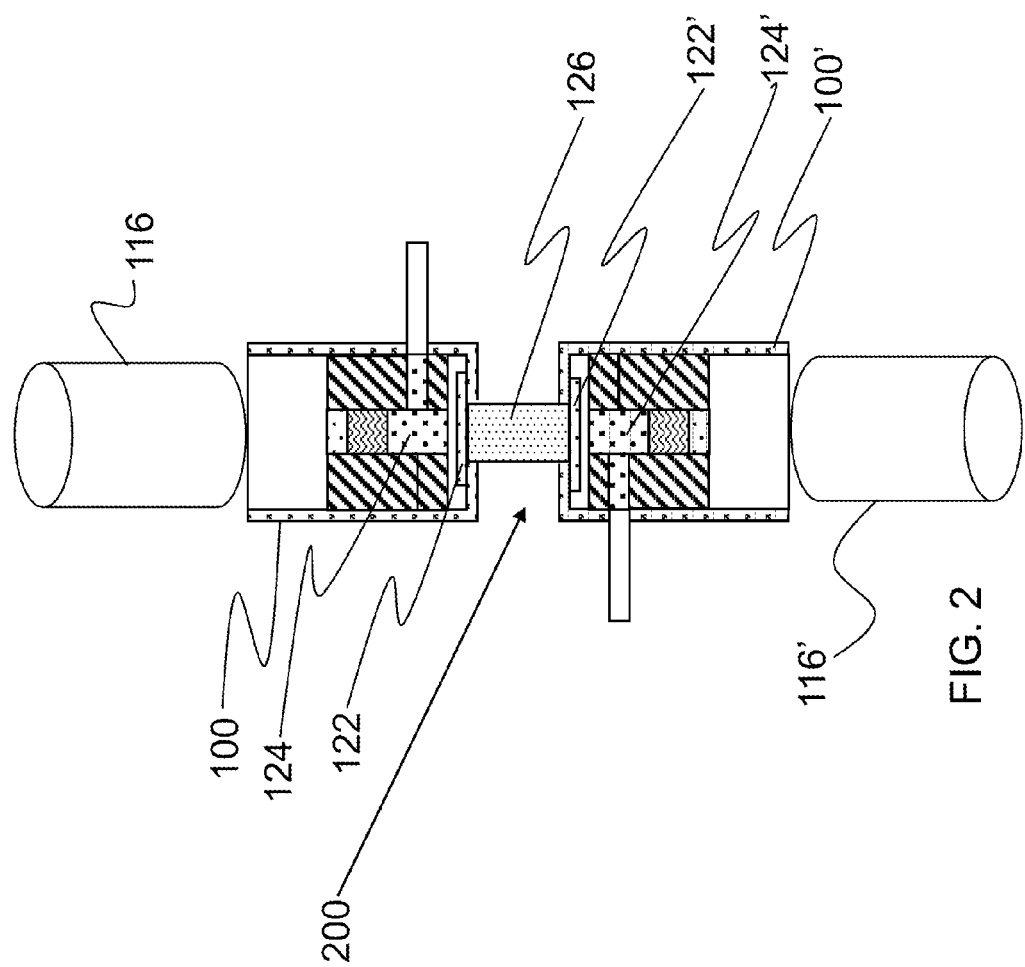
FIG. 2 is an illustration of an embodiment of the transmission/echo mode device of the present invention employing two of the basic units used in series for sending and/or receiving signals.

FIG. 2 is an illustration of an embodiment of the apparatus of the invention. The embodiment consists of a pair of test devices 100 and 100' used in transmission mode 200. Each test device houses an ultrasonic transducer 124 and 124' and protects it from damage while transferring forces from the external loading frames 116 and 116' to the specimen 126 or vice versa. In transmission mode, the ultrasonic wave from a shear transducer 124 passes through the adjacent spacer 122, the specimen 126, the second spacer 122', and ultimately reaches the receiving ultrasonic transducer 124'; in echo mode, as shown in FIG. 1. The device in FIG. 2 may also be operated in echo mode, the ultrasonic wave from a transducer 124 passes through the adjacent spacer 122, the specimen 126, and reflects from the far edge of the specimen, then travels back through the specimen, the spacer 122 and finally reaches the emitting ultrasonic transducer 124 that produced the wave or another, receiver transducer (not shown) that is proximate with the wave-producing transducer. As can be appreciated by one of ordinary skill in the art, although the above examples use shear transducers to produce the ultrasonic waves, longitudinal wave or surface wave transducers or combinations of any these would also be suitable. One of ordinary skill in the art can also appreciate that, in transmission mode, either transducer can be used as either the sender or receiver and can detect reflections as well.

Figure 3:
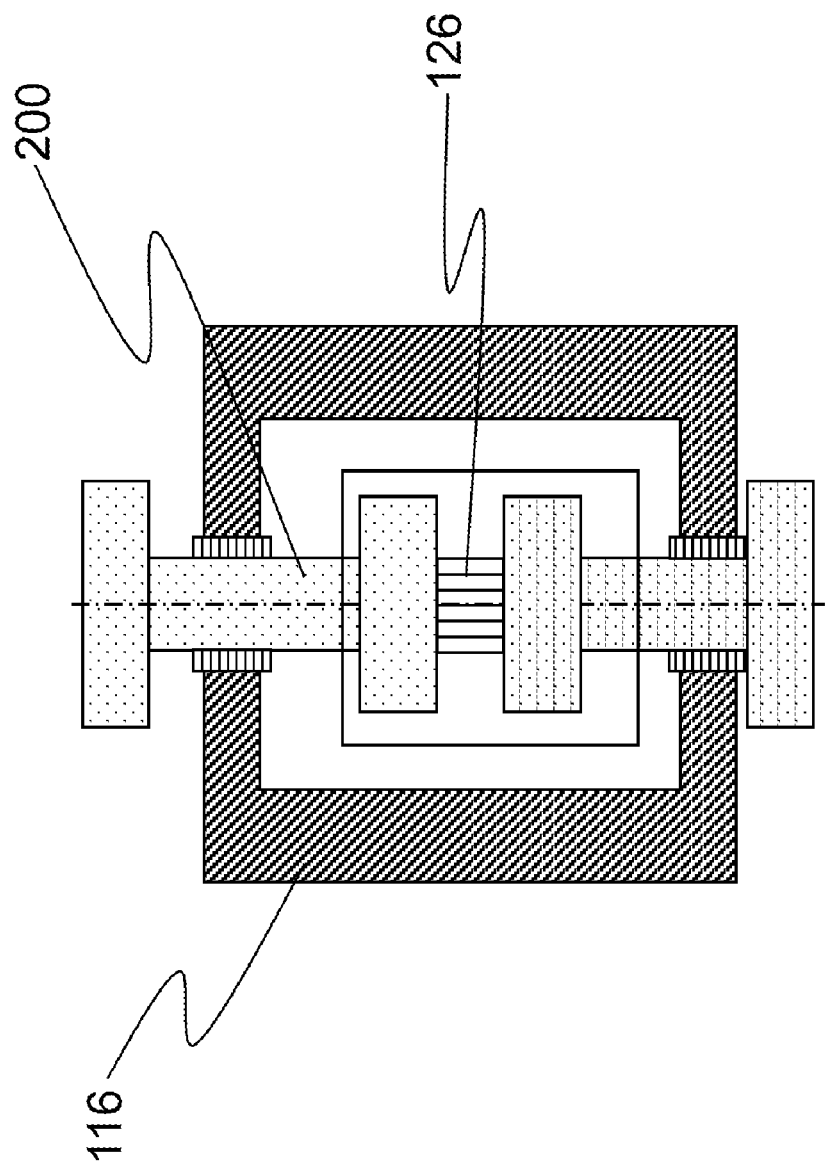
FIG. 3 is an illustration of one example of the transmission/echo mode device of the present invention connected with an external load frame.

FIG. 3 is an illustration of the device of the present transmission used in transmission mode 200 and inserted into an external load frame 116 which loads the specimen 126.

Figure 4:
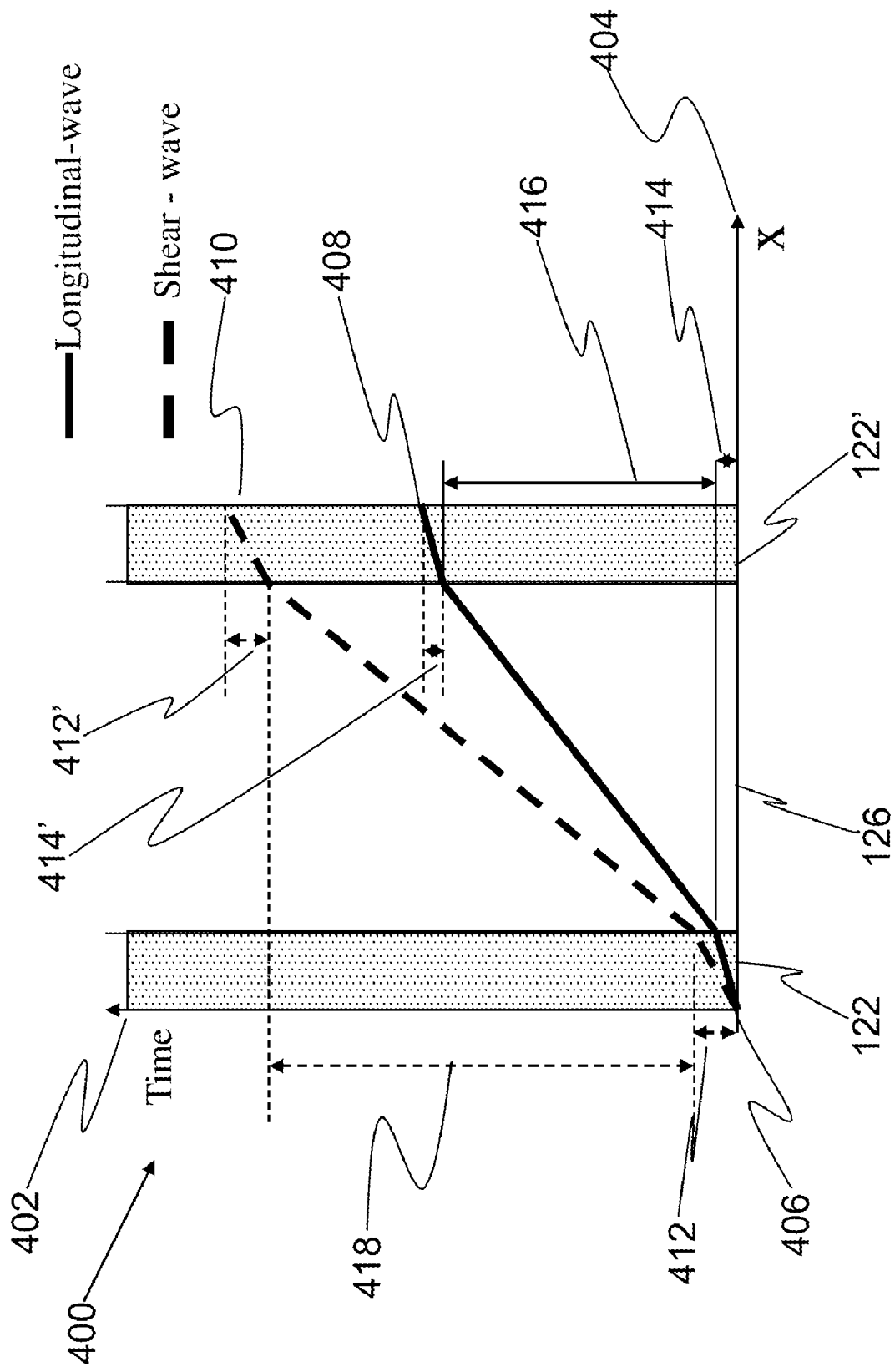
FIG. 4 is a schematic diagram depicting the propagation of longitudinal and shear waves through various portions of the transmission mode device of the present invention.

FIG. 4 shows a schematic 400 of wave propagation for the device of the present invention used in transmission mode (as shown in FIG. 2 and FIG. 3). In the setup used, spacer 122 and spacer 122' oppose one anther. In this case, the first spacer 122 is proximate to the sending ultrasonic transducer 124 and the spacer 122' proximate to the receiving ultrasonic transducer (not shown). The specimen 126 is between the two ultrasonic transducers (not shown) and the spacers 122 and 122'. The time axis 402 increases vertically toward the top on the page and the distance axis 404 increases horizontally toward the right on the page. At the start of the experiment 406, an ultrasonic pulse of either shear or longitudinal type is launched from the sender ultrasonic transducer. Mode conversion at the spacer 122 makes both a shear pulse and a longitudinal pulse, which continue to propagate through the sample 126 and second spacer 122' but at different speeds. The longitudinal pulse (solid line) arrival occurs at the receiver transducer at 408, and the shear pulse (dashed line) arrival occurs at the receiver transducer at 410. Since the longitudinal wave speed and shear wave speed in the spacers are known, the thickness of the spacers are known, and any angles of incidence are known (or can be calculated by one of ordinary skill in the art), the spacer longitudinal delays 412 and 412' can be calculated by one of ordinary skill in the art. Likewise, the spacer shear delays 414 and 414' can also be calculated. With this information, one of ordinary skill in the art can calculate the specimen longitudinal delay 416 and the specimen shear delay 418.

Figure 5:
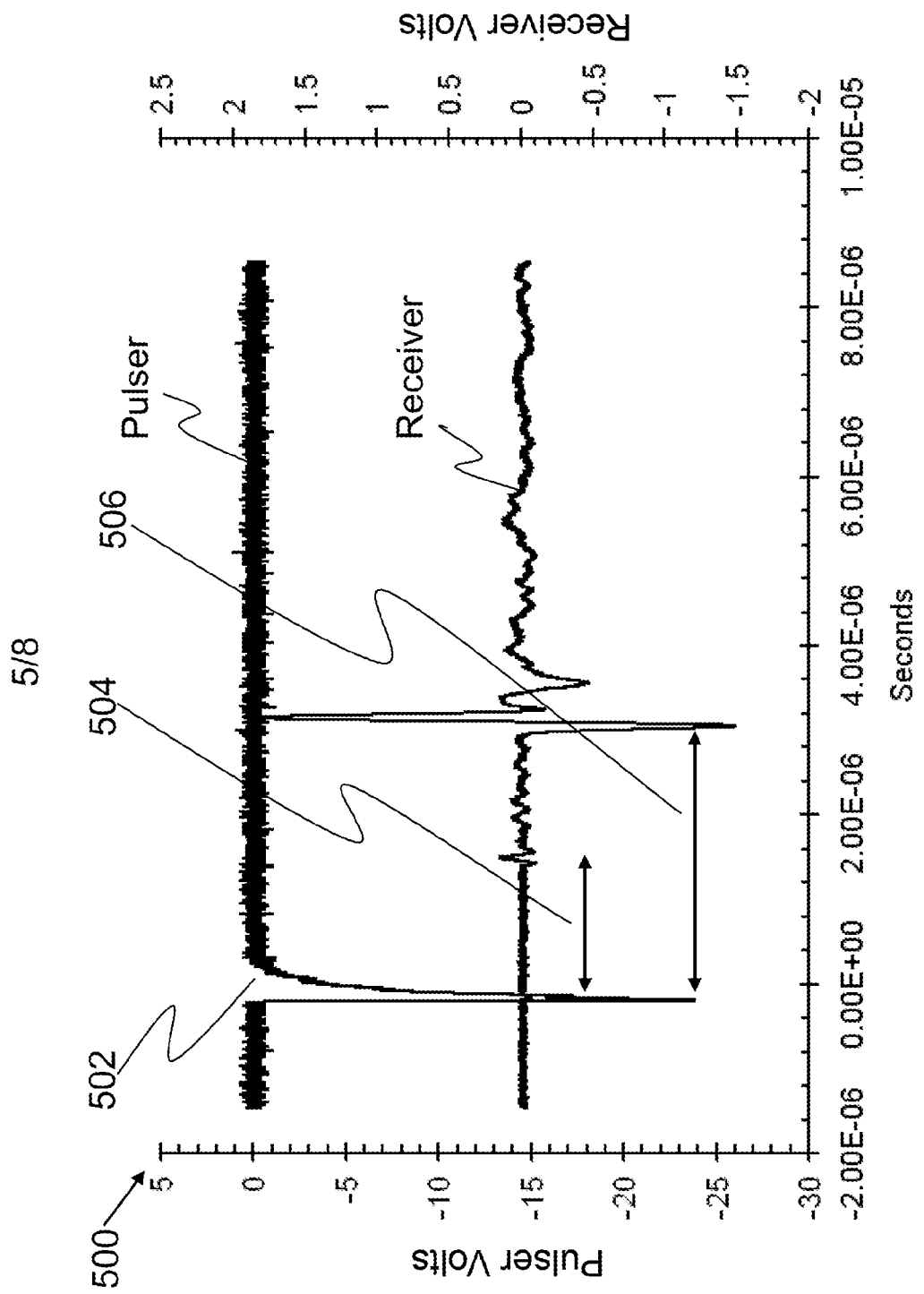
FIG. 5 is a time series showing realistic data of what a typical device of the present invention would detect after having launched a shear wave pulse into a sample.

FIG. 5 is a graph depicting typical experimental data using the device of the present invention in conjunction with an oscilloscope connected with ultrasonic transducers. One of ordinary skill in the art can appreciate that many types of data collection apparatus exist for such experiments. An ultrasonic pulse 502 is launched at on the pulser transducer/sender transducer. A leading transmission group, the longitudinal pulse, arrives after an effective longitudinal delay 504. A trailing transmission group, the shear pulse, arrives after an effective shear delay 506.

Figure 6:
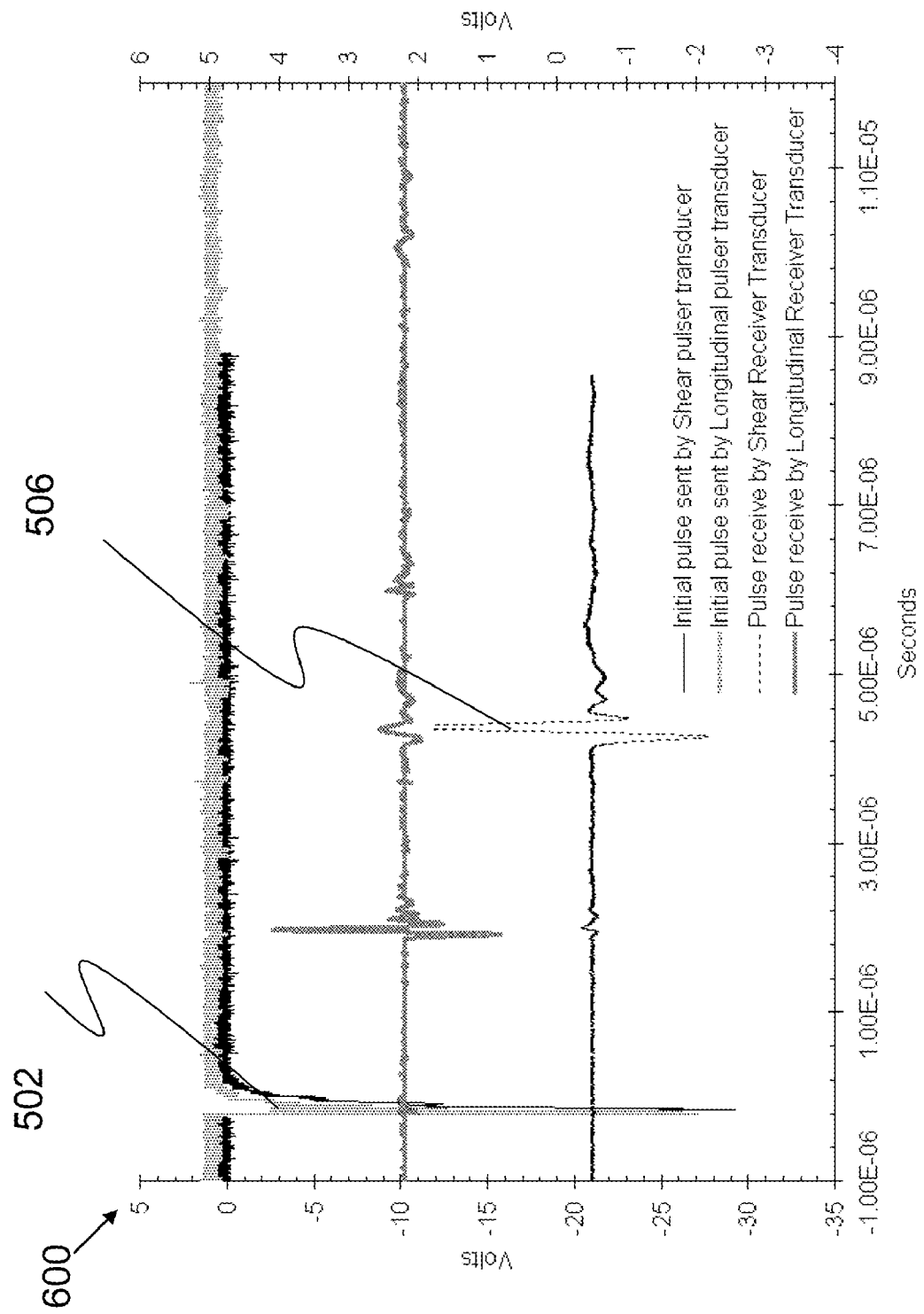
FIG. 6 is a time series showing realistic data of what a typical device of the present invention in echo/transmission mode would see having launched both shear wave and longitudinal wave pulses into a sample.

FIG. 6 is a graph of the signal output 600 from a set of transducers in the device, the device operating in transmission mode. It is clear that the first peak in the shear signal 506 corresponds directly to the arrival of the longitudinal wave. This confirms that both the longitudinal and shear wave speeds can be measured simultaneously.

Figures 7A, 7B:
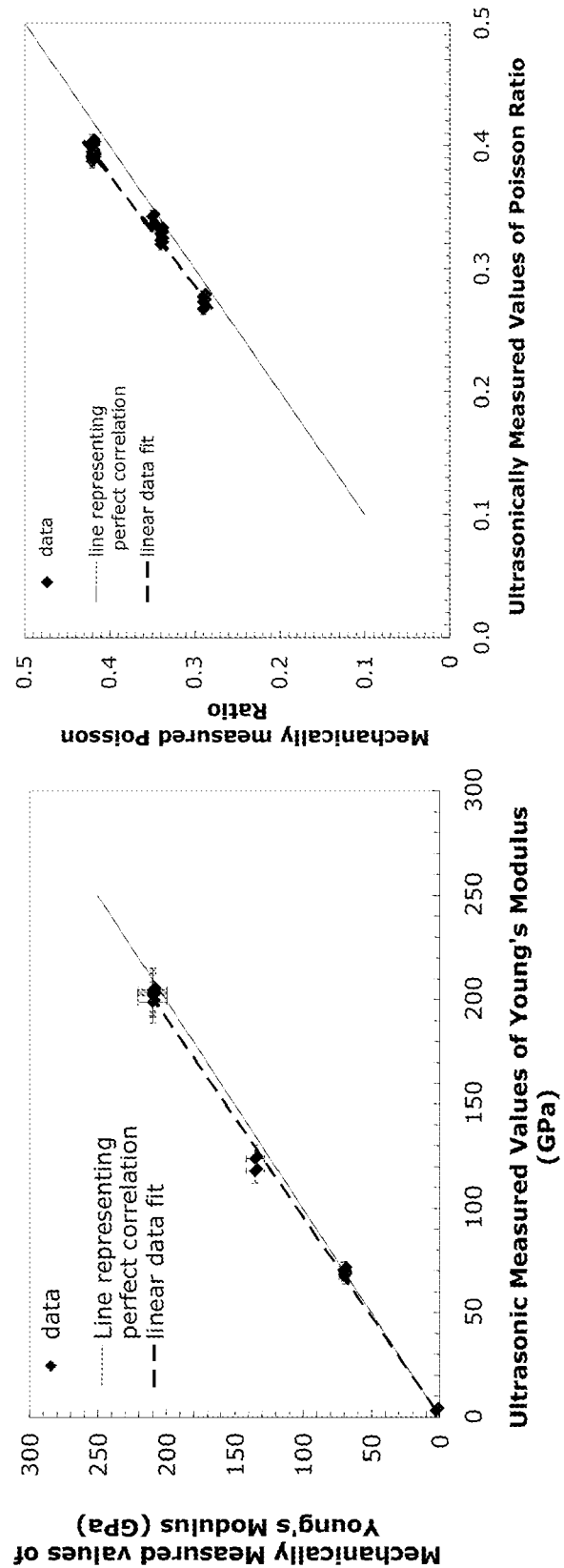
FIG. 7a is a plot showing a comparison of the Young's modulus of several materials measured with the device of the present invention and a standard mechanical technique/device for measuring Young's modulus.
FIG. 7b is a plot showing a comparison of the Poisson's ratio of several materials measured with the device of the present invention and a standard mechanical technique/device for measuring Young's modulus.

FIG. 7a is a plot showing the results of mechanical tests performed using a Materials Testing System (MTS) to compare the mechanically measured Young's modulus to the ultrasonically measured Young's modulus. Validation of the experimental setup was conducted on specimens of steel, polycarbonate, copper, and aluminum. The results of these tests demonstrate that the mechanically measured and ultrasonically measured values of Young's Modulus agree.

FIG. 7b is a plot showing a comparison of the calculated Poisson ratio with respect to standard values of Poisson ratio. The results of these tests demonstrate that the device accurately determines the Poisson ratio of the material.

Figure 8B:
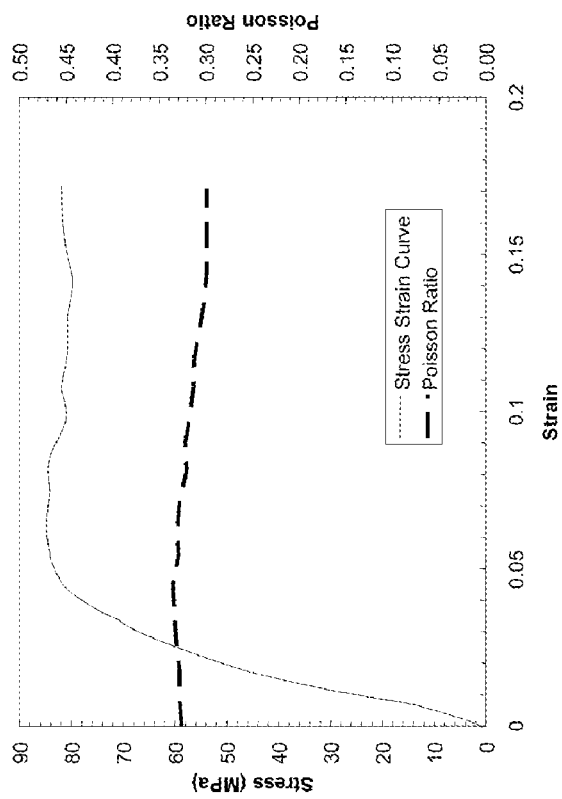
FIG. 8b is a plot of realistic data using the device of the present invention of a material under uniaxial load from which the Poisson's ratio is extracted.
Figure 8A:
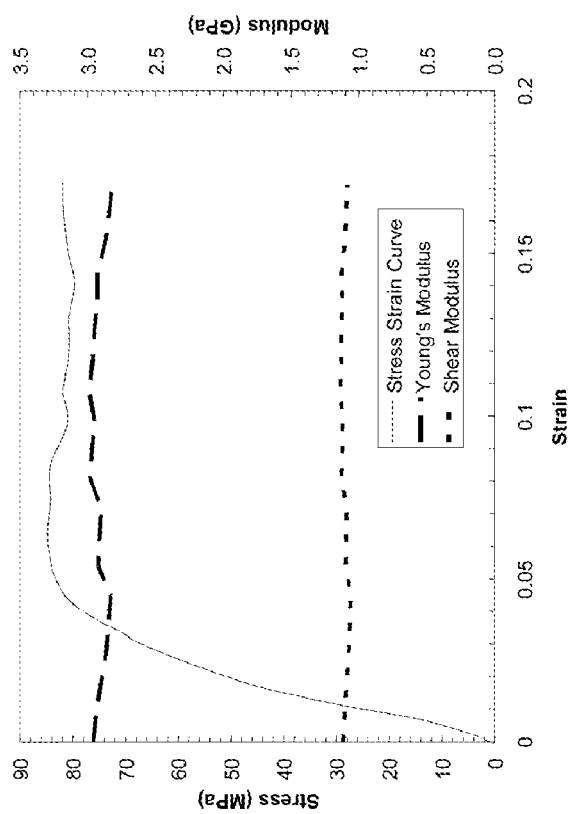
FIG. 8a is a plot of realistic data using the device of the present invention of a material under uniaxial load from which the Young's modulus is extracted.

The ability of the device to measure the material constants during compression was also tested. Theoretically, the Young's modulus and Poisson ratio of polycarbonate materials should not change during compression through the plastic regime. Experimental results on a polycarbonate are plotted in FIG. 8a and FIG. 8b. FIG. 8a demonstrates that the Young's modulus and shear modulus remain constant throughout the elastic plastic regime. FIG. 8b demonstrates that the Poisson ratio also remains constant throughout the elastic plastic regime.

The casing may be made of a ceramic or heat-resistant material to protect the device from heat effects, thereby allowing for high temperature ultrasonic compression testing of materials. The device can also house different types of sensors and although the present invention has been discussed as it relates to ultrasonic transducers a variety of other acoustic emission detectors for measuring acoustic emissions during compression may be substituted. While specific materials and configurations have been discussed, they have been provided to serve as examples only and are not intended to limit the scope of the present invention.

In conclusion, the innovative techniques introduced herein are the simultaneous measurements of longitudinal and shear wave speeds using only shear transducers or only longitudinal transducers and the ability to measure the ultrasonic wave speed in a load train during compression tests without damaging the ultrasonic test device.

What is claimed is:

1. An apparatus for simultaneously measuring longitudinal and shear wave speeds in materials under load comprising:
    a rigid housing with a long axis, a body substantially parallel to the long axis with an exterior surface and an interior surface, an open end, a closed end substantially opposite the open end with a hole in the closed end extending through the interior surface and the exterior surface, the closed end substantially perpendicular to the long axis, and a housing exit port in the body of the rigid housing extending through the interior surface and the exterior surface;
    a spacer residing inside the rigid housing, the spacer having a spacer specimen side and a spacer transducer side substantially parallel to the spacer specimen side, the spacer substantially larger than the hole in the closed end of the rigid housing, the spacer further contacting the interior surface of the rigid housing such that the closed end of the housing is in contact with the spacer specimen side;
    a load transferring body fitting substantially inside the rigid housing, the load transferring body having an exterior, the entirety of the exterior of the load transferring body making substantially close contact with the interior surface of the body of the rigid housing, the load transferring body further having a transducer hole extending fully through the load transferring body and substantially parallel to the long axis of the rigid housing, the load transferring body further having a load transferring body exit port extending from the transducer hole fully through the load transferring body;
    an ultrasonic transducer fitting substantially inside the transducer hole of the load transferring body; and
    a transducer depressing mechanism, the transducer depressing mechanism securing the ultrasonic transducer against the spacer transducer side.

2. An apparatus as set forth in claim 1, wherein another, identical device is opposite the device.

3. An apparatus as set forth in claim 1, wherein the rigid housing is a right-circular cylinder, the load transferring body is a right-circular cylinder, and the spacer is a right-circular cylinder.

4. An apparatus as set forth in claim 1, wherein the transducer depressing mechanism is a spring inserted into the transducer hole of the load transferring body such that the ultrasonic transducer is between the spring and the spacer, and the device further comprises a set-screw, the set-screw removably threaded into the transducer hole of the load transferring body, whereby the set-screw is adjusted to compress the spring against the ultrasonic transducer, holding the ultrasonic transducer firmly against the spacer transducer side.

5. An apparatus as set forth in claim 1, the device further comprising a set screw removably threaded into the transducer hole of the load transferring body.

6. An apparatus as set forth in claim 1, wherein the ultrasonic transducer is a shear wave transducer.

7. An apparatus as set forth in claim 1, wherein the ultrasonic transducer is a longitudinal wave transducer.

* * * * *